(12) United States Patent
Nycz et al.

(10) Patent No.: US 7,833,269 B2
(45) Date of Patent: Nov. 16, 2010

(54) OSTEOCHONDRAL IMPLANT PROCEDURE

(75) Inventors: Jeffrey H. Nycz, Collierville, TN (US);
Daniel Shimko, Germantown, TN (US);
Jeetendra Bharadwaj, Memphis, TN (US)

(73) Assignee: Warsaw Orthopedic, Inc

( * ) Notice: Subject to any disclaimer, the term of this patent is extended or adjusted under 35 U.S.C. 154(b) by 1185 days.

(21) Appl. No.: 11/339,194

(22) Filed: Jan. 25, 2006

(65) Prior Publication Data
US 2007/0172506 A1     Jul. 26, 2007

(51) Int. Cl.
A61F 2/08     (2006.01)
A61F 2/38     (2006.01)

(52) U.S. Cl. .............. 623/14.12; 623/20.16; 623/906
(58) Field of Classification Search ............. 623/908, 623/14.12, 20.16, 23.58; 264/222
See application file for complete search history.

(56) References Cited

U.S. PATENT DOCUMENTS

| | | | | |
|---|---|---|---|---|
| 4,249,975 A | * | 2/1981 | Rechenberg | 156/245 |
| 4,600,551 A | * | 7/1986 | Erb | 264/222 |
| 4,645,503 A | * | 2/1987 | Lin et al. | 623/23.58 |
| 5,501,706 A | * | 3/1996 | Arenberg | 623/23.56 |
| 6,042,608 A | * | 3/2000 | Ishikawa et al. | 623/7 |
| 6,059,831 A | * | 5/2000 | Braslow et al. | 128/898 |
| 6,451,139 B1 | * | 9/2002 | Weber-Unger et al. | 156/61 |
| 2002/0016636 A1 | * | 2/2002 | Ricci et al. | 623/23.51 |
| 2003/0216669 A1 | * | 11/2003 | Lang et al. | 600/587 |
| 2003/0220700 A1 | * | 11/2003 | Hammer et al. | 623/23.58 |
| 2005/0222687 A1 | * | 10/2005 | Vunjak-Novakovic et al. | 623/23.63 |
| 2005/0234549 A1 | * | 10/2005 | Kladakis et al. | 623/14.12 |
| 2005/0251266 A1 | * | 11/2005 | Maspero et al. | 623/23.51 |

FOREIGN PATENT DOCUMENTS

| | | |
|---|---|---|
| DE | 19713305 A1 * | 10/1998 |
| WO | WO 9921497 A1 * | 5/1999 |

OTHER PUBLICATIONS

U.S. Appl. No. 11/340,024, filed Jan. 26, 2006, Nycz et al.
U.S. Appl. No. 11/338,926, filed Jan. 25, 2006, Bharadwaj et al.
U.S. Appl. No. 11/317,985, filed Dec. 23, 2005, Lyons.
U.S. Appl. No. 11/340,884, filed Jan. 27, 2006, Shimko et al.
U.S. Appl. No. 11/343,156, filed Jan. 30, 2006, Bharadwaj et al.
U.S. Appl. No. 11/339,694, filed Jan. 25, 2006, Gil.

* cited by examiner

*Primary Examiner*—Bruce E Snow
*Assistant Examiner*—Melissa Hoban

(57) ABSTRACT

The present disclosure includes a surgical kit for preparing a damaged area of a human knee to receive at least one graft. The kit includes a moldable material positioned over the damaged area to form a template. Desirably, a tape is placed over the template and cut to correspond to a template area so that the tape is used to determine the number and/or a dimension of the openings and the number and/or dimension of a corresponding graft to be inserted into each opening. The graft is adhered to a surface of the tape.

14 Claims, 2 Drawing Sheets

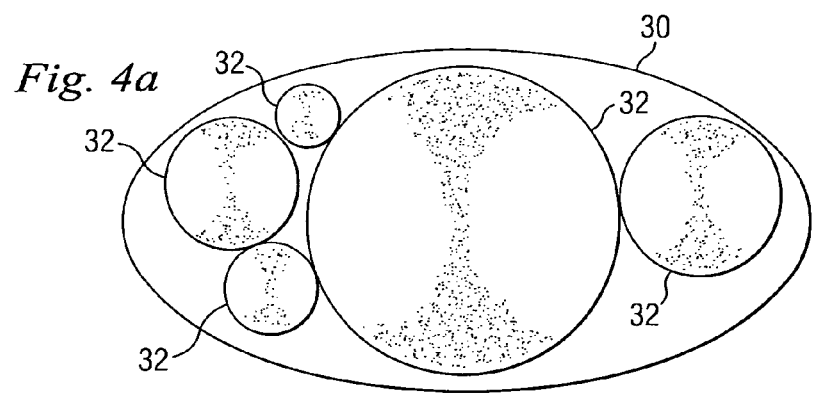
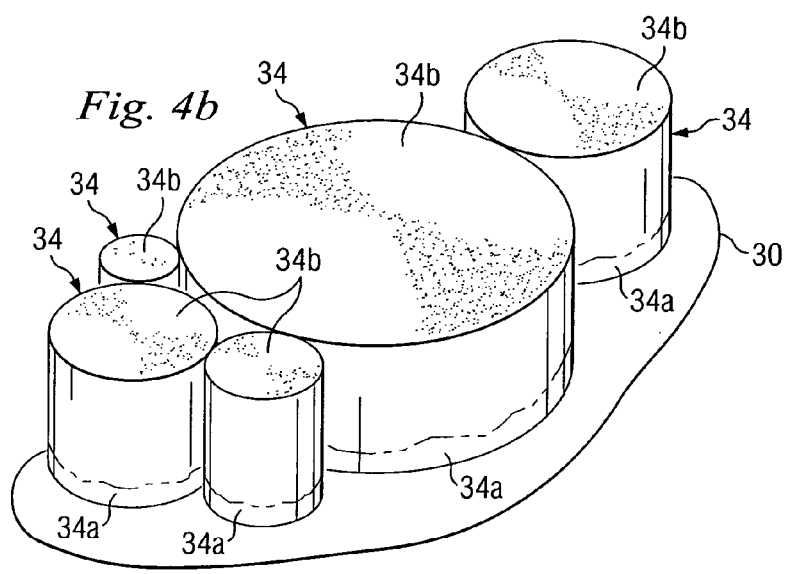
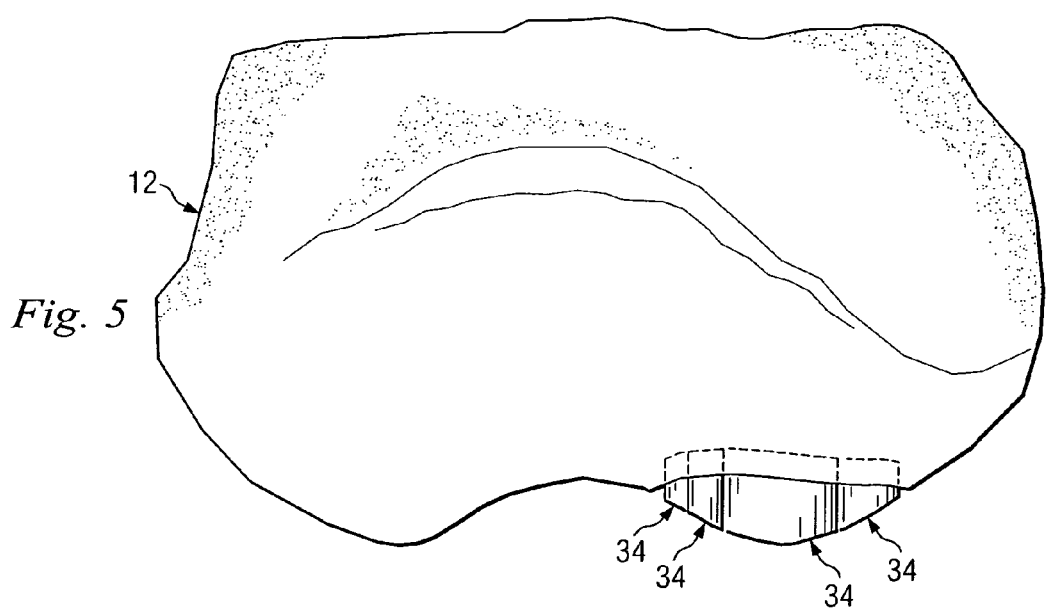

OSTEOCHONDRAL IMPLANT PROCEDURE

BACKGROUND

This invention relates to an improved osteochondral implant procedure, and more particularly, to such a procedure in which one or more recipient openings are form in the anatomy for receiving a graft.

In the human body, the knee consists of three bones—a femur, a tibia, and a patella—that are held in place by various ligaments. The corresponding chondral areas of the femur and the tibia form a hinge joint, and the patella protects the joint. Portions of the chrodral areas, as well as the underside of the patella, are covered with an articular cartilage, which allow the femur and the tibia to smoothly glide against each other without causing damage.

The articular cartilage often tears, usually due to traumatic injury (often seen in athletics) and degenerative processes (seen in older patients). This tearing does not heal well due to the lack of nerves, blood vessels and lymphatic systems; and the resultant knee pain, swelling and limited motion of the bone(s) must be addressed.

Damaged cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, the known artificial prostheses have largely been unsuccessful since they are deficient in the elastic, and therefore in the shock-absorbing, properties characteristic of the cartilage. Moreover, the known artificial devices have not proven able to withstand the forces inherent to routine knee joint function.

In an attempt to overcome the problems associated with the above techniques, osteochondral transplantation, also known as "mosaicplasty" has been used to repair articular cartilages. This procedure involves removing injured tissue from the damaged area and drilling openings in the underlying bone. One or more implants, or grafts, consisting of healthy cartilage overlying bone, are obtained from another area of the patient, typically from a lower weight-bearing region of the joint under repair, or from a donor patient, and are implanted in the openings.

Since the geometry of the defect is often complex, it is often difficult to perfectly match the dimensions of the grafts(s) to those of the openings(s). Also, in the case of relatively large defects requiring multiple grafts, it is often difficult to determine, in advance of harvesting, the size and number of grafts that are needed. Therefore what is needed is a procedure to ameliorate these difficulties.

BRIEF DESCRIPTION OF THE DRAWING

FIG. 4a is a plan view of a tape showing an outline of the location of a series of grafts.

FIG. 4b is a plan view of the tape of FIG. 4a supporting the series a grafts.

FIG. 5 is a view similar to that of FIG. 2, but depicting the grafts of FIG. 4b implanted in the femur.

DETAILED DESCRIPTION

Figure 1:
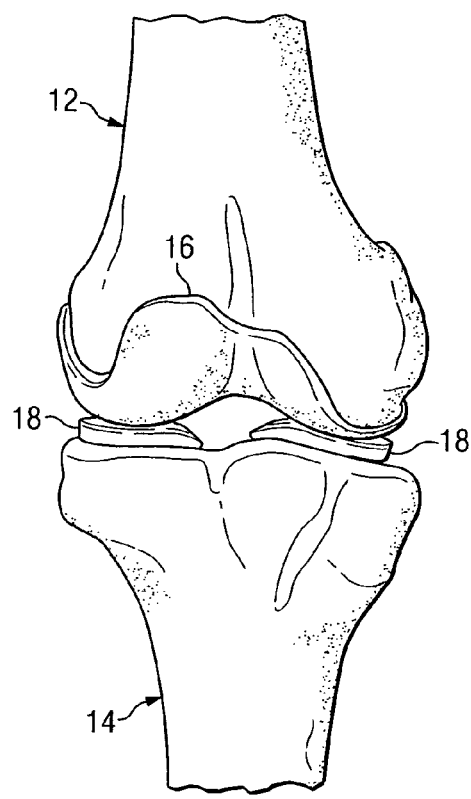
FIG. 1 is an elevational view of a human knee with certain parts removed in the interest of clarity.

Referring to FIG. 1 there is illustrated, in general, a knee area of a human including a femur 12 and a tibia 14 whose respective chondral areas are in close proximity. A cartilage 16 extends over a portion of the chondral area of the femur 12, and a meniscus 18 extends between the cartilage and the tibia 14. The patella, as well as the tendons, ligaments, and quadriceps that also form part of the knee are not shown in the interest of clarity.

Figure 2A:
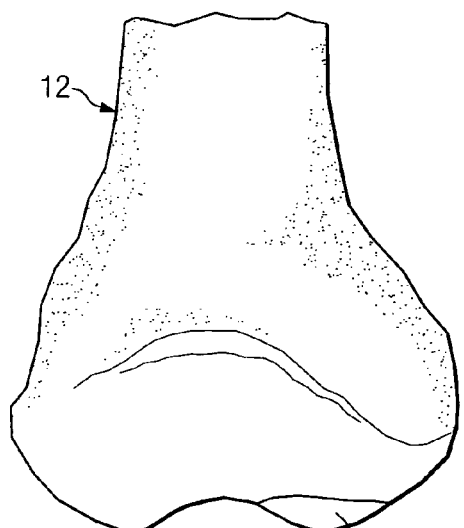
FIG. 2a is an enlarged elevational view of the femur of the knee of FIG. 1.

FIG. 2a depicts a defect, or void, 12a in the femur 12 of FIG. 1. In this context, it will be assumed that at least a portion of the defect 12a was created as a result of a portion of the cartilage 16 extending over a chrondral area of the femur 12 wearing away or becoming damaged and being removed by the surgeon. It also will be assumed that the defect 12a also includes a portion of the condyle that extended immediately below the worn or removed cartilage.

According to an embodiment of the procedure of the present invention, an opening, or series of openings, are formed in the femur 12 that extend from the defect 12a into the corresponding condyle of the femur to receive a correspond number of grafts, or plugs (not shown in FIG. 1 or 2a). It is understood that one or more of these grafts are harvested from another area of the patient/recipient, such as an undamaged non-load bearing area of the femur or tibia, or from a corresponding area of a donor, in accordance with known techniques. These grafts are sized so as to be implantable in the above openings in accordance with the following procedure.

Figure 3:
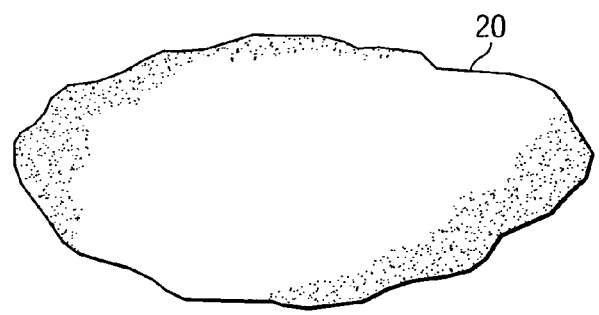
FIG. 3 is an enlarged plan view of the mold of FIG. 2b.
Figure 2B:
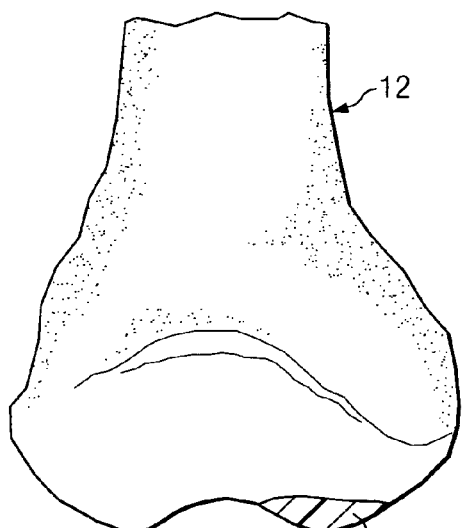
FIG. 2b is a view similar to that of FIG. 2 but depicting a mold associated with the femur.

Referring to FIG. 2b, a mold 20 is initially formed by placing a moldable material, such as silicone, or the like, in the defect 12a and allowing it to harden. The mold 20 is then removed from the defect and placed on an operating table, or the like, as shown in FIG. 3, and one of several additional procedures can then take place.

For example, the mold 20 can be used as a template to determine the dimension and number of implants, or grafts, to be formed in the damaged area with a relatively low amount of spacing between the grafts. In other words, using the mold as a guide, the cross-sectional areas of the openings, and therefore the grafts, are selected so as to have a relatively low amount of space between the implanted grafts. For the purposes of this application, the expression "relatively low" means that the amount of unoccupied space in the area of the defect 12a is less than the amount of the area that is occupied by the grafts. Ideally, the selection is such that a minimum amount of space exists between the implanted grafts.

For example, using the mold 20 as a guide or template, one or more grafts having a relatively large diameter, can initially be selected; and then other, relatively small, grafts could be selected as needed to fill in the remaining portion of the defect 12a so as to achieve a relatively low, and preferably minimum, amount of spacing between the grafts when implanted in the defect. It is understood that the grafts could be harvested and selected from a bank of grafts of varying dimensions, or the grafts could be harvested after their dimensions have been determined in accordance with the above.

Referring to FIG. 4a, according to another technique, a tape is placed over the lower surface of the mold 20 and cut to conform to the area of the lower surface of the mold, with the cut portion of the tape being referred to by the reference numeral 30. Then, the number of grafts and their corresponding cross-sectional areas (in the example shown, diameters)

are determined in order to obtain a maximum fill of the defect 12a and thus insure a relatively low, and preferably a minimum, amount of spacing between the grafts. These grafts are outlined on one surface of the tape as shown by the reference numeral 32 in FIG. 4a. In the example shown, the outlines 32 are of five grafts having circular cross-sections of varying diameters.

Referring to FIG. 4b, a series of grafts 34 are then harvested, or otherwise obtained, with the dimensions of the cross-sections of the grafts corresponding to those of the outlines 32 of FIG. 4a. Each graft consists of a cartilage portion 34a overlying a chrondral portion 34b.

It is understood that adhesive can be placed on the corresponding surface of the tape 30 and/or on the outer surface of each cartilage portion 34a of each graft 34 so that, when the cartilage portions are placed on the tape 30 with the cartilage portions 34a engaging the tape as shown in FIG. 4b, the grafts 34 will adhere to the tape.

Referring to FIG. 5, a series of openings are then drilled in the condyle of the femur 12 extending from the bottom surface of the defect 12a into the condyle. The diameters of the openings and the spacing between the openings are based on the outlines 32. The assembly, consisting of the grafts 34 adhered to the tape 30, is then brought to the vicinity of the defect 12a and the other ends of the chrondral portions 34b of the grafts 34 are inserted in the respective openings. The grafts 34 are then completely implanted in the openings. The depths of the openings and the lengths of the grafts 34 are such that, when implanted, the upper surfaces of the cartilage portions 34a of the grafts 34 extend flush with the upper surface of the undamaged cartilage 16 on the femur 12. It is understood that the diameters of the openings, when compared to the diameters of the grafts 34 (and therefore the outlines), are such that the grafts fit in the openings in a relatively tight fit.

As a result, a maximum fill of the defect 12a with the grafts 34 is obtained, with a relatively low, and preferably a minimum, amount of spacing between the grafts.

It is understood that a surgical kit can be provided consisting of the above moldable material and some tape. The moldable material is applied over the defect 12a to form the mold 20 that is used as a template as described above, and the tape is cut from the template to form the cut portion 30, and is used in the manner described above to determine the number and/or dimensions of the openings to be formed in the damaged area for receiving grafts. Adhesive can be provided that is placed on the corresponding surface of the tape 30, or on the grafts 34 as discussed above, so that, when the cartilage portions are placed on the tape 30 with the cartilage portions 34a engaging the tape as shown in FIG. 4b, the grafts 34 will adhere to the tape.

VARIATIONS

1. The number, shape and dimensions of the grafts, and therefore the corresponding openings that receive the grafts, can vary within the scope of the invention.

2. The sequence of the steps disclosed above can be changed within the scope of the invention. For example, the sequence of the drilling of the holes and the harvesting of the grafts can be reversed.

3. The cross-section of one or more of the grafts can be other than circular. For example they can be elliptical, square, rectangular, triangular, or take any other polygonal shape.

4. The spatial references mentioned above, such as "upper", "lower", "under", "over", "between", "outer", "inner" and "surrounding" are for the purpose of illustration only and do not limit the specific orientation or location of the components described above.

5. It is understood that, although in each of the embodiments a series of grafts are discussed, the defect may be of a size that only one graft is necessary.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A surgical kit for preparing a damaged area of a human knee to receive at least one graft, the kit comprising:
   a moldable material configured to fit over the damaged area to form a mold that is configured as a template of the damaged area, the template including an area;
   a tape cut in a configuration and dimension corresponding to the template area;
   at least one graft harvested from a biological sample configured to fit in at least one opening formed in the damaged area based on the configuration and dimension of the tape, wherein the number and/or dimension of the at least one graft is based on the configuration and dimension of the tape, wherein the at least one graft is adhered to a first surface of the tape.

2. The kit of claim 1 wherein the dimension of each opening is a cross-sectional area of the opening.

3. The kit of claim 2 wherein each opening and its corresponding graft has a circular cross-section.

4. The kit of claim 1 wherein the at least one opening includes a plurality of openings formed for receiving a corresponding number of grafts, and wherein cross-sectional areas of the openings are selected so as to have a relatively low amount of space between the implanted grafts.

5. The kit of claim 1 wherein the at least one opening includes a plurality of openings formed for receiving a corresponding number of grafts, and wherein cross-sectional areas of the openings are selected so as to have a minimum amount of space between the implanted grafts.

6. The kit of claim 1 wherein the at least one graft includes a chondral portion disposed for engagement with the damaged area and a cartilage portion disposed for engagement with the tape.

7. The kit of claim 1 wherein the at least one opening is drilled into the damaged area and the said at least one graft is configured to fit within at least one opening drilled into the damaged area so that it can be inserted therewith in a tight fitting engagement.

8. The kit of claim 1 wherein the at least one graft includes a plurality of grafts, the grafts having varying dimensions.

9. An osteochondral implant kit comprising:
   a mold configured to correspond to a damaged osteochondral area, the mold defining a template surface;
   a tape configured to correspond to the template surface; and
   at least one implant harvested from a biological sample configured to fit in at least one opening formed in the damaged area based on the configuration and dimension of the tape, wherein the number and/or dimension of the at least one implant is based on the configuration and dimension of the tape, wherein the at least one implant is adhered to a first surface of the tape.

10. The kit of claim 9 wherein the at least one opening includes a plurality of openings formed for receiving a corresponding number of implants, and wherein cross-sectional areas of the openings are selected so as to have a relatively low amount of space between the implants.

11. The kit of claim 9 wherein the at least one opening includes a plurality of openings formed for receiving a corresponding number of implants, and wherein cross-sectional areas of the openings are selected so as to have a minimum amount of space between the implants.

12. The kit of claim 9 wherein the at least one implant includes a chondral portion disposed for engagement with the damaged osteochondral area and a cartilage portion disposed for engagement with the tape.

13. The kit of claim 9 wherein the at least one opening is drilled into the damaged osteochondral area and the at least one implant is configured for insertion therewith in a tight fitting engagement.

14. The kit of claim 9 wherein the at least one implant includes a plurality of implants, the implants having varying dimensions.

* * * * *